（12) United States Patent
Willis

(10) Patent No.: US 9,435,758 B2
(45) Date of Patent: Sep. 6, 2016

(54) BIDIRECTIONAL BALLAST

(75) Inventor: Peter M. Willis, Benton Harbor, MI (US)

(73) Assignee: Leco Corporation, St. Joseph, MI (US)

( * ) Notice: Subject to any disclaimer, the term of this patent is extended or adjusted under 35 U.S.C. 154(b) by 794 days.

(21) Appl. No.: 13/550,098

(22) Filed: Jul. 16, 2012

(65) Prior Publication Data

US 2013/0023057 A1 Jan. 24, 2013

Related U.S. Application Data

(60) Provisional application No. 61/509,227, filed on Jul. 19, 2011.

(51) Int. Cl.
*G01N 25/22* (2006.01)
*G01N 25/26* (2006.01)
*G01N 31/12* (2006.01)
*G01N 33/28* (2006.01)
*G01N 1/44* (2006.01)

(52) U.S. Cl.
CPC ............ *G01N 25/26* (2013.01); *G01N 1/44* (2013.01); *G01N 31/12* (2013.01); *G01N 33/2829* (2013.01)

(58) Field of Classification Search
CPC ........ G01N 31/12; G01N 1/22; G01N 1/405; G01N 1/44; G01N 5/04; G01N 33/2829; G01N 1/04; G01N 1/2258; G01N 5/00; G01N 31/005; G01N 33/1846; G01N 33/241
USPC ..................................... 436/155, 160; 422/78
See application file for complete search history.

(56) References Cited

U.S. PATENT DOCUMENTS

| | | | |
|---|---|---|---|
| 3,369,459 A * | 2/1968 | Fisher | ................................ 91/39 |
| 4,622,009 A | 11/1986 | Bredeweg | |
| 6,270,727 B1 | 8/2001 | Mitchell et al. | |
| 6,291,802 B1 | 9/2001 | Ford | |
| 7,070,738 B2 | 7/2006 | Mitchell et al. | |
| 7,497,991 B2 | 3/2009 | Rohaly et al. | |
| 2004/0171165 A1* | 9/2004 | Mitchell et al. | ............... 436/155 |

* cited by examiner

*Primary Examiner* — Lyle Alexander
*Assistant Examiner* — Dwan A Gerido
(74) *Attorney, Agent, or Firm* — Price Heneveld LLP

(57) ABSTRACT

An analyzer with a combustion furnace includes a flow path of byproducts of combustion coupled to a bidirectional ballast chamber by valves which are sequentially actuated for alternately filling and exhausting byproducts of combustion from opposite sides of the chamber during combustion. Alternately, a plurality of low volume ballast chambers are employed. A method of determining the concentration of elements in a sample includes the steps of combusting a sample; and alternately collecting and exhausting the byproduct gases of combustion in opposite sides of a bidirectional ballast. The bidirectional ballast chamber has an outer wall defining a chamber with sealed enclosures at opposite ends of the wall, a movable piston positioned within the chamber, and gas ports associated with the chamber on opposite sides of the piston.

7 Claims, 4 Drawing Sheets

BIDIRECTIONAL BALLAST

CROSS-REFERENCE TO RELATED APPLICATIONS

This application claims priority under 35 U.S.C. §119(e) and the benefit of U.S. Provisional Application No. 61/509,227 entitled BIDIRECTIONAL BALLAST, filed on Jul. 19, 2011, by Peter M. Willis, the entire disclosure of which is incorporated herein by reference.

BACKGROUND OF THE INVENTION

The present invention relates to elemental analyzers and particularly an analyzer employing one or more bidirectional ballasts for the collection of analytes. The new ballast system extends the range and performance capabilities of existing ballast-type CHN(S) organic instruments.

The determination of elements, such as carbon, hydrogen, and nitrogen, in an organic material is desirable for numerous reasons. In recent years, the food market has become interested in determining the amount of protein in a sample which can be determined by the nitrogen content. Thus, the determination of nitrogen is important in providing useful information to the nutritional market. The carbon-to-hydrogen ratio is desirable in the characterization of coal and coke samples, as are the carbon, hydrogen, and nitrogen ratios in a variety of other organic materials. Thus, elemental analyzers have been in use for these and other applications for some time.

In present organic combustion analyzers, such as a TruSpec® analyzer from Leco Corporation of St. Joseph, Mich., oxygen ($O_2$) gas is passed through a high temperature furnace. The sample material is positioned in the furnace for combustion and subsequent analysis. The combustion gases are captured in movable piston ballast, typically 6 liters in volume and the gasses are pressurized to approximately 1.5 atm. After equilibration in the ballast, the gasses are exhausted through a 10 cc aliquot loop which is subsequently equilibrated at atmospheric pressure. This process results in approximately a 1/900 portion of the combustion gases sent on for further analysis. The balance of the collected gasses is exhausted without being analyzed. This system is described in U.S. Pat. No. 7,070,738, assigned to the present assignee, the disclosure of which is incorporated herein by reference. U.S. Pat. Nos. 7,497,991; 4,622,009; 6,291,802; and 6,270,727 also disclose components of a combustion system which can be employed in the system of the present invention. The disclosures of the '991, '009, '802, and '727 patents are also incorporated herein by reference.

In these elemental analyzers, the contents of the aliquot loop are transferred into a helium stream where water ($H_2O$) and carbon dioxide ($CO_2$) are measured using non-dispersive IR detector (NDIR) cells. Finally nitrogen ($N_2$) is measured using a thermal conductivity (TC) cell. Because the TC cell is a non-discriminant detector, all other gases from combustion must first be scrubbed before measuring $N_2$. A small aliquot loop is desirable because, if large doses were used, the scrubbers would have to be replaced much more often incurring cost and downtime.

The prior art leaves room for improvement. Initially, the ballast is sized for the upper range of the sample size and concentration. As a result, very small or low concentration samples may be over-diluted with $O_2$ limiting the low end of the detected dynamic range of samples. The constant ballast volume also limits the high end because, once the ballast is filled, no additional gas can be collected. Also, the recovery of substances that combust more slowly (i.e., longer than the time to fill the ballast) may not occur. The analysis time is also fixed, based upon purge time of the furnace; the fill, equilibrate, and exhaust times of the large ballast; and upon the fill, equilibrate, and scrubbing times of the aliquot dose.

SUMMARY OF THE INVENTION

The disclosed invention overcomes the above limitations by continuously alternately filling opposite sides of a small bidirectional ballast (or alternately filling a plurality of small ballasts) with the combustion gases during combustion of a sample, allowing the analysis to be divided into several small sections. While one side of the small ballast is filling, the gas from the alternate ballast filling is exhausted through a small aliquot doser volume. The aliquot is then transferred into a helium stream for analysis. The ratio of ballast volume to aliquot volume can remain at 900:1 such that no more scrubber gas is consumed than in the former ballast system.

Dividing the analysis into multiple small sections prevents low concentration materials from being over-diluted. Also, the number of sections is not limited so the analysis time of high concentration or slowly combusting material can be extended as needed. The ballast fillings can commence just prior to the sample material being dropped into the furnace. These initial ballast samplings can provide a real-time blank measurement if desired. On previous instruments with a large ballast a complete analysis sequence is required to measure blanks. By continuously detecting the gasses during the combustion period, the analysis time can be automatically adjusted to conserve $O_2$ and scrubbing reagents. Also, the total analysis time can be significantly reduced because the collecting and analyzing steps overlap.

This invention includes an analyzer with a combustion furnace for receiving samples for combustion. A flow path of byproducts of combustion from the combustion furnace is coupled to a bidirectional ballast chamber by valves which are sequentially actuated for alternately filling and exhausting byproducts of combustion from the chamber during combustion.

The invention also contemplates a method of determining the concentration of elements in a sample including the steps of combusting a sample; and alternately collecting and exhausting the byproduct gases of combustion in opposite sides of a bidirectional ballast or in multiple low volume ballasts.

This invention also is a bidirectional ballast chamber for an analyzer having an outer wall defining a chamber with sealed enclosures at opposite ends of the wall, a movable piston positioned within the chamber, and gas ports associated with said chamber on opposite sides of the piston.

These and other features, objects and advantages of the present invention will become apparent upon reading the following description thereof together with reference to the accompanying drawings.

DETAILED DESCRIPTION OF THE PREFERRED EMBODIMENT

Figure 1:
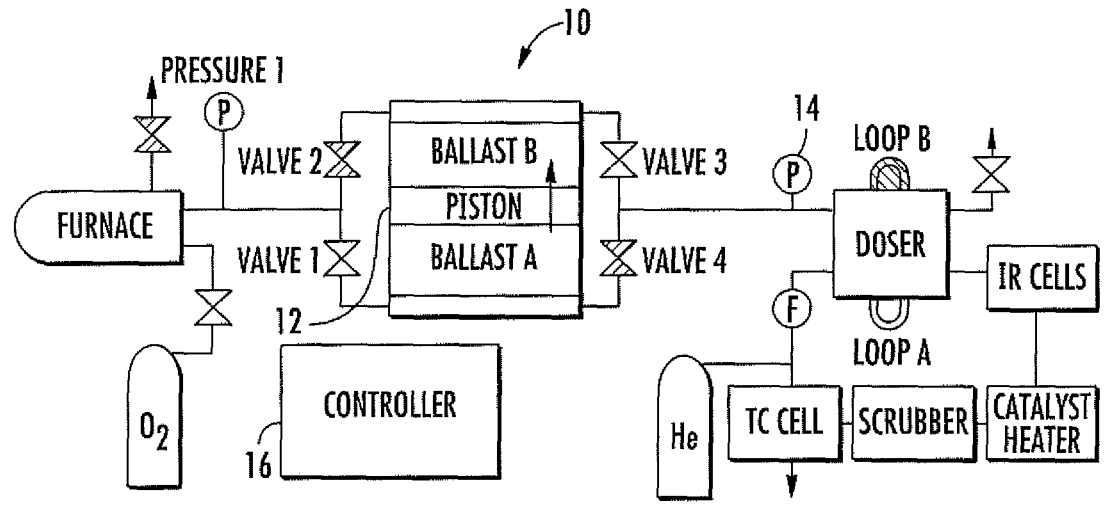
FIG. 1 is a schematic diagram of a combustion system in which a bidirectional ballast chamber is employed.
Figure 2:
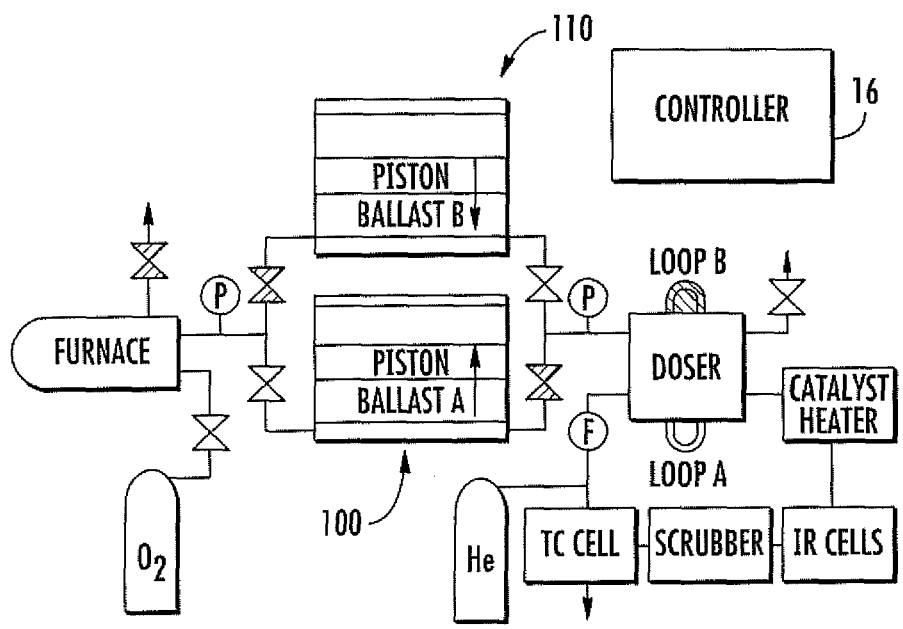
FIG. 2 is a schematic diagram of a combustion system in which two independent ballast chambers are employed.

Referring initially to FIG. 1, which is the preferred embodiment, there is shown a single bidirectional ballast chamber 10. FIG. 2 is an alternate embodiment employing two small, low volume, independent ballast chambers 100 and 110. In FIG. 1, as Ballast A is filling with byproducts of combustion, the piston 12 separating chambers A and B moves to the top end of the ballast 10. During this time, Ballast B is exhausting through Dose Loop B. Once the dead-stop is encountered at the end of the piston stroke, a predetermined pressure increase in the furnace pressure is detected by detector 14. The aliquot will have a short equilibration time during this over-filling. The pressure rise will trigger the controller 16, which is conventionally coupled to each of the valves and sensors, to change the valve states to begin filling ballast B. At the same time the closer is toggled dumping the contents of Dose Loop B into the helium stream and permitting filling Dose Loop A with the exhaust of Ballast A.

The system of FIG. 2 operates in a similar manner using a pair of relatively small, low volume (about 0.5 liter) ballast chambers 100 and 110. In both systems, the controller 16 controls the sliding gate valves 1-4 and their states as shown in FIGS. 4-6, and each of the ballast chambers A and B are filled and exhausted from 5-20 times to capture the analytes during a combustion cycle.

Combustion will occur slightly above atmospheric pressure resulting in less demand on furnace seals. The ballast piston 12 will have $O_2$ on both sides allowing the area between the piston o-rings to equilibrate to $O_2$. The furnace ballasts and aliquot loops are self-purging because the analysis continues until baseline (blank level) is once again reached indicating that the lines are free from combustion contaminants. The next analysis can commence as soon as the baseline is reached on the current analysis.

Figure 3:
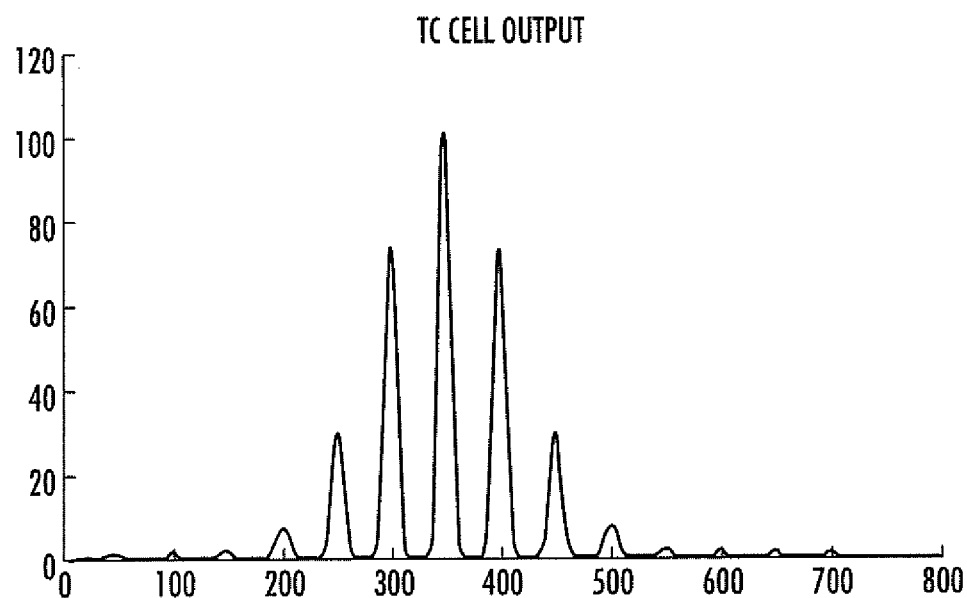
FIG. 3 is a pictorial diagram of a thermal conductivity cell output showing nitrogen detected during successive aliquot samples during a combustion cycle for the combustion system shown in FIGS. 1 and 2.
Figure 4:
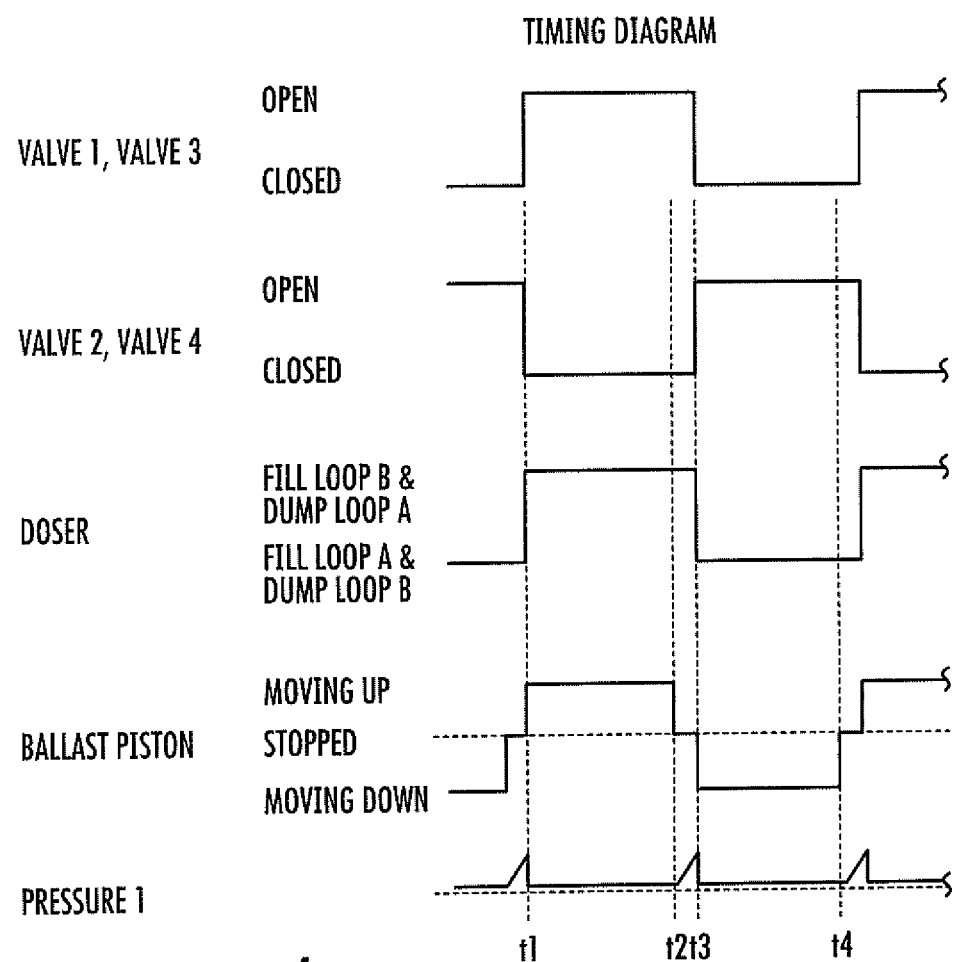
FIG. 4 is a timing diagram showing the control of the valves employed with the ballast chamber shown in FIGS. 1 and 2 during two of the many sampling cycles.
Figure 5A:
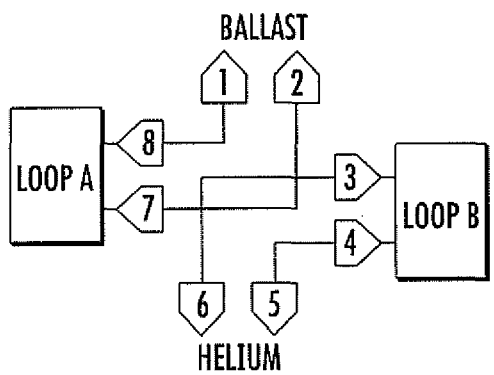
FIGS. 5A-5D are schematic diagrams of the sliding gate valves and flow paths for controlling the filling of ballast A and dumping of ballast B in FIGS. 1 and 2.
Figure 5B:
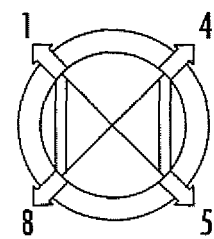
Figure 5C:
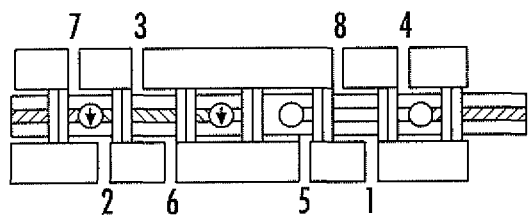
Figure 5D:
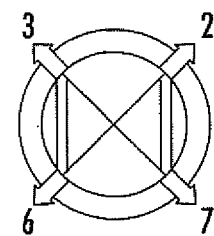
Figure 6A:
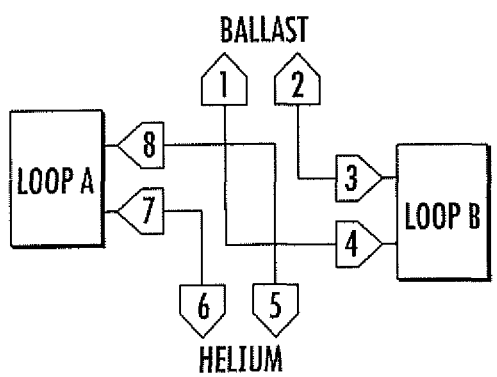
FIGS. 6A-6D are schematic diagrams and schematics of the sliding gate valves and flow paths for the filling of ballast B and the dumping of ballast A in FIGS. 1 and 2.
Figure 6B:
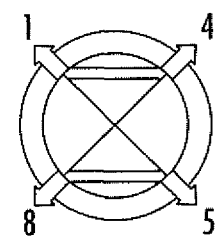
Figure 6C:
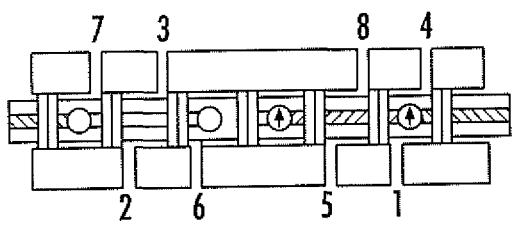
Figure 6D:
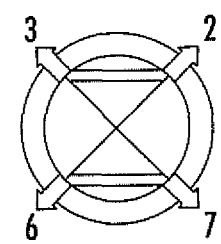

FIG. 4 is a timing diagram showing the control of the valves employed with the ballast chamber shown in FIGS. 1 and 2 during two of the many sampling cycles;

FIGS. 5A-5D are schematic diagrams of the sliding gate valves and flow paths for controlling the filling of ballast A and dumping of ballast B in FIGS. 1 and 2;

FIGS. 6A-6D are schematic diagrams and schematics of the sliding gate valves and flow paths for the filling of ballast B and the dumping of ballast A in FIGS. 1 and 2; and An analysis begins with one or multiple blank doses and then the sample is introduced into the combustion furnace. The intermediate peaks will vary in height as the analysis proceeds and return to the blank level after combustion is over. The two ballasts and dose loops A and B are self-cleaned eliminating the purging presently required to prepare for the next analysis. FIG. 3 shows a TC Cell output for the system. The individual peaks are integrated by the controller 16 coupled to the valves and detection cells to provide a total nitrogen readout. The NDIR sensors provide similar signals representing the hydrogen and carbon content of a sample present during combustion. The burn time for the equivalent of a 4.5 liter ballast is approximately 1.5 minutes. If the analysis is divided into 9 sections, each section will last approximately 10 seconds.

Figure 7:
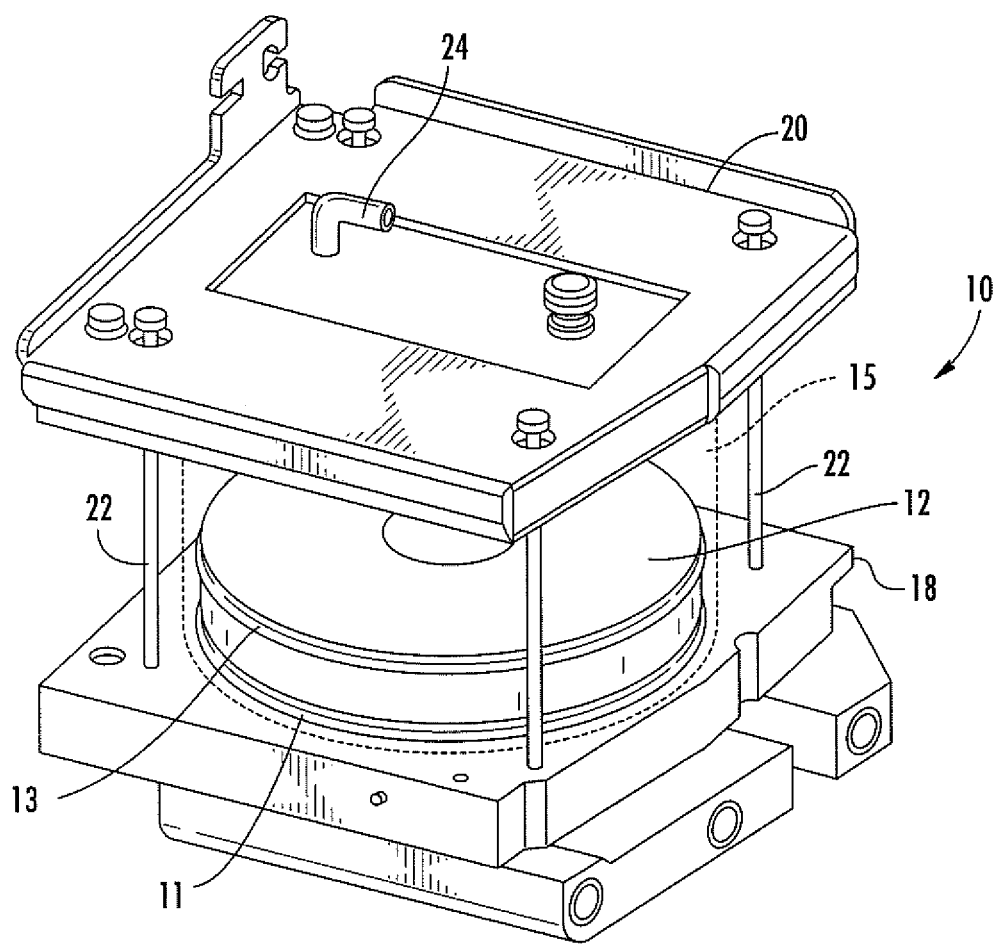
FIG. 7 is a perspective view of the bidirectional ballast chamber.

FIG. 7 shows a typical relatively small bidirectional ballast chamber 10, which can be employed in connection with the system of the present invention. The ballast chamber includes a cylindrical glass outer wall 15 with sealed end plates 18 and 20 supported in spaced and sealed relationship to wall 15 by a plurality of supports 22. Gas inlet and outlet ports for each of the end plates 18 and 20, as shown schematically in FIG. 1, are sealed gas connections, such as connection 24 shown in FIG. 7. The chamber includes a floating disk-shaped piston 12 with dual, spaced-apart O-rings 11 and 13. Piston 12 divides chamber 10 into opposite sides (A and B) and is shown in FIG. 7 in the lowered position, in which ballast volume A is being exhausted and ballast volume B above piston 12 is filled.

The following is a summary of the advantages of the systems shown in FIGS. 1 and 2:
Faster analysis (<½ time)
Less $O_2$ (typically <½) used reducing the cost of an analysis—analysis dictates amount, operator does not have to predict as necessary with variable fill ballast
Fewer reagents (<½) required leading to lower cost analysis
Larger dynamic range (Low level and high level)—not limited by ballast size at high end or dilution at low end
Improved signal-to-noise ratio with less dilution
Smaller ballast—smaller package footprint
Very fast blanks, auto-blanks before and after analysis.
Faster purge time—system is self-cleaning
Ballast piston equilibrates to $O_2$ between O-rings
Lower pressure combustion The system can use existing control circuits to control valves and measure pressure. Existing TC or IR cell assemblies can be used as the detectors as can temperature controllers for the ballast(s) and doser oven. The software LabView™, commercially available from Leco Corporation of St. Joseph, Mich., can control the system and collect data. A dual rotary doser or dual linear doser can be employed. A small oven holds the ballast chamber(s). Two 0.5 liter ballasts or a 3" diameter×5" length 0.5 liter ballasts can be employed. The system can connect to a Leco Model No. FP628 or TruMac® controller to evaluate combustion analysis. In some systems, a plurality (more than two) of the relatively low volume ballast chambers may be employed and controlled to sequentially fill and dump samples into the doser.

It will become apparent to those skilled in the art that, given the teaching of this specification, multiple bidirectional or unidirectional ballasts may be employed to achieve the improved performance of an analyzer. It will also be apparent to those skilled in the art that these and other modifications can be made without departing from the spirit or scope of the invention as defined by the appended claims.

The invention claimed is:
1. An analyzer comprising:
a combustion furnace for receiving gaseous samples for combustion;
a flow path of gaseous byproducts of combustion from said combustion furnace;
a bidirectional ballast chamber having a piston dividing said chamber into first and second sections; and valves coupling said ballast chamber to said combustion furnace and to the flow path of gaseous combustion byproducts, said valves coupled to said combustion furnace and said ballast chamber to fill said first section of said chamber and exhaust said second section of said chamber as said piston is moved in a first direction and fill said second section and exhaust said first section as said piston moves in an opposite direction for alternately filling and exhausting gaseous byproducts of combustion from said first and second sections of said chamber.

2. A method of determining the concentration of elemental elements in a sample including the steps of:
combusting a sample; and
alternately collecting and exhausting the byproduct gases of combustion in two separate sections on opposite sides of a piston in a bidirectional ballast, wherein said collecting step further includes sequentially actuating valves associated with said bidirectional chamber to alternately fill and exhaust said sections on opposite sides of said piston.

3. A bidirectional ballast chamber for collecting combustion byproducts from a furnace and supplying collected samples to an analyzer comprising:
an outer wall defining a chamber;
enclosures at opposite ends of said wall;
a movable piston positioned within said chamber to divide said chamber into two gas collecting sections;
a pair of gas ports associated with said chamber on each of the opposite sides of said piston; and
valves coupled to said gas ports for alternately filling and exhausting combustion byproducts from the furnace into said gas collecting sections and out to the analyzer, respectively.

4. The chamber as defined in claim 3 wherein said wall is cylindrical.

5. The chamber as defined in claim 4 wherein said piston is disk-shaped.

6. The chamber as defined in claim 5 wherein said piston includes a pair of spaced-apart sealing O-rings.

7. The chamber as defined in claim 6 and further including a controller coupled to said valves for alternately actuating said valves to sequentially fill and exhaust gases on opposite sides of said piston.

* * * * *